United States Patent
Zawadzki et al.

(10) Patent No.: US 9,744,248 B2
(45) Date of Patent: *Aug. 29, 2017

(54) CREPED PREBIOTIC TISSUE

(71) Applicant: Kimberly-Clark Worldwide, Inc., Neenah, WI (US)

(72) Inventors: Michael Andrew Zawadzki, Roswell, GA (US); Jeffrey Janne Johnson, Neenah, WI (US); David William Koenig, Menasha, WI (US); Amy Lynn Vanden Heuvel, Hortonville, WI (US); David Andrew Moline, Appleton, WI (US); Rebecca Ann Vongsa, Neenah, WI (US); Cathleen Mae Uttecht, Menasha, WI (US); Donald Eugene Waldroup, Roswell, GA (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/367,331

(22) Filed: Dec. 2, 2016

(65) Prior Publication Data
US 2017/0080105 A1    Mar. 23, 2017

Related U.S. Application Data

(63) Continuation of application No. 14/766,087, filed as application No. PCT/US2014/058372 on Sep. 30, 2014.

(51) Int. Cl.
| | |
|---|---|
| A61K 31/733 | (2006.01) |
| B31F 1/12 | (2006.01) |
| A61K 47/48 | (2006.01) |
| D21H 27/00 | (2006.01) |
| D21H 21/14 | (2006.01) |
| A61K 31/19 | (2006.01) |
| A61F 2/04 | (2013.01) |

(52) U.S. Cl.
CPC ........ *A61K 47/48976* (2013.01); *A61K 31/19* (2013.01); *A61K 31/733* (2013.01); *A61K 47/48207* (2013.01); *B31F 1/12* (2013.01); *B31F 1/126* (2013.01); *D21H 21/146* (2013.01); *D21H 27/00* (2013.01); *D21H 27/002* (2013.01); *A61F 2/04* (2013.01); *A61F 2002/045* (2013.01)

(58) Field of Classification Search
CPC ........... A61F 13/15577; A61F 13/8405; A61L 15/44; A61L 15/46; A61L 15/60; A61L 2300/232
See application file for complete search history.

(56) References Cited

U.S. PATENT DOCUMENTS

| | | |
|---|---|---|
| 7,025,974 B2 | 4/2006 | Farmer et al. |
| 7,332,179 B2 | 2/2008 | Kistler et al. |
| 7,642,395 B2 | 1/2010 | Schroeder et al. |
| 8,110,215 B2 | 2/2012 | Koenig et al. |
| 8,506,978 B2 | 8/2013 | Soerens et al. |
| 8,552,251 B2 | 10/2013 | Zhou et al. |
| 2003/0185811 A1 | 10/2003 | Teasdale et al. |
| 2005/0112239 A1 | 5/2005 | Rudin et al. |
| 2007/0036776 A1 | 2/2007 | Reid et al. |
| 2007/0178202 A1 | 8/2007 | Verbruggen et al. |
| 2007/0275129 A1 | 11/2007 | Pershad et al. |
| 2008/0206188 A1 | 8/2008 | Alverdy et al. |
| 2009/0181157 A1 | 7/2009 | Toreki et al. |
| 2011/0002984 A1 | 1/2011 | Atkin et al. |
| 2012/0035277 A1 | 2/2012 | Davis |
| 2012/0058181 A1 | 3/2012 | Currie et al. |
| 2012/0164200 A1 | 6/2012 | Qin et al. |
| 2012/0269865 A1 | 10/2012 | Roughead et al. |
| 2012/0328586 A1 | 12/2012 | Lang et al. |
| 2013/0004540 A1 | 1/2013 | O'Mahony et al. |
| 2013/0065967 A9 | 3/2013 | Benjamin et al. |
| 2013/0137643 A1 | 5/2013 | Zimmer et al. |
| 2013/0281948 A1 | 10/2013 | Ehrnsperger et al. |
| 2014/0096924 A1 | 4/2014 | Rekoske et al. |
| 2015/0080826 A1 | 3/2015 | Ehrnsperger et al. |
| 2015/0209468 A1 | 7/2015 | Aviles et al. |

FOREIGN PATENT DOCUMENTS

| | | |
|---|---|---|
| CN | 102370598 A | 3/2012 |
| CN | 102871921 A | 1/2013 |
| DE | 27 38 652 A1 | 3/1979 |
| GB | 2 495 491 A1 | 4/2013 |
| WO | WO 2004/017979 A2 | 3/2004 |
| WO | WO 2005/115171 A1 | 12/2005 |
| WO | WO 2010/123419 A1 | 10/2010 |
| WO | WO 2012/118535 A1 | 9/2012 |

*Primary Examiner* — Audrea Buckley
(74) *Attorney, Agent, or Firm* — Kimberly-Clark Worldwide, Inc.

(57) ABSTRACT

The invention relates to creped prebiotic tissue products. The tissue products comprise prebiotics in sufficiently high amounts to have a prebiotic effect in use, without negatively affecting tissue product properties, such as tensile strength, stiffness or softness. Thus, in certain embodiments the present invention provides soft, durable creped prebiotic tissue products that are able to improve the growth of healthy bacteria such as *Bifidobacterium* spp. or *Lactobacillus* spp. without promoting growth of enteropathogenic bacteria. The tissue products provide these benefits yet have a GMT greater than about 500, a Stiffness Index less than about 20 and a TS7 value less than about 10.

18 Claims, 1 Drawing Sheet

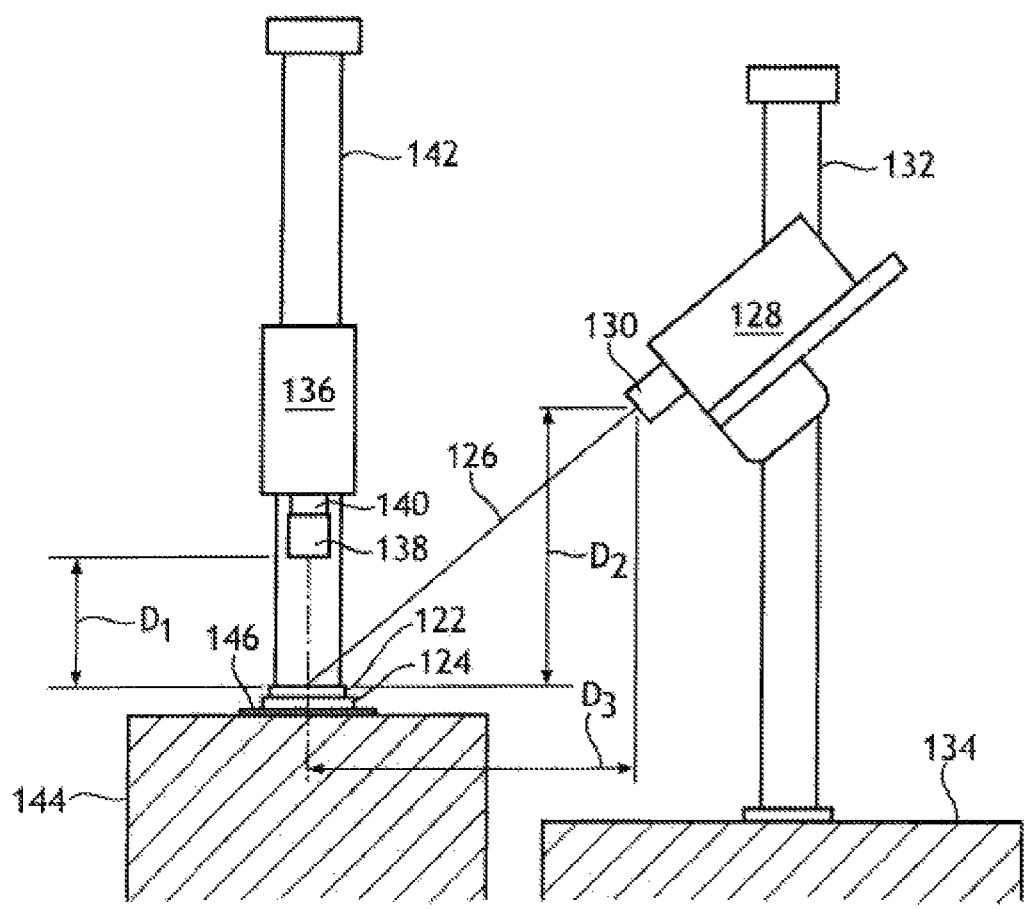

CREPED PREBIOTIC TISSUE

RELATED APPLICATIONS

The present application is a continuation application and claims priority to U.S. patent application Ser. No. 14/766,087, filed on Aug. 5, 2015, which is a national-phase entry, under 35 U.S.C. §371, of PCT Patent Application No. PCT/US14/58372, filed on Sep. 30, 2014, which is incorporated herein by reference in a manner consistent with the instant application.

BACKGROUND OF THE DISCLOSURE

Gastrointestinal health is a major concern of consumers, driving demand for products that can be consumed on a daily basis to improve gastrointestinal health. One example of consumables that may improve gastrointestinal health is a class of compounds known in the art as prebiotics. Typically, prebiotics are non-digestible polysaccharides such as fructans and fructo-oligosaccharides. Prebiotics are typically administered as food components and have a beneficial health effect through their selective metabolism in the intestinal tract. Prebiotics commonly target intestinal bacteria such as bifidobacteria and lactobacilli, stimulating their growth and activity and improving intestinal health through the production of short chain fatty acids and antimicrobial compounds that target pathogens. While prebiotic food stuffs are useful in improving gastrointestinal health, the requirement that they be consumed orally is a limitation. Therefore, there remains a need for alternate forms of administration of prebiotics.

Tissue manufactures have employed polysaccharides in the manufacture of creped tissue products with some success. The polysaccharides however, have generally been limited to digestible polysaccharides such as modified and unmodified starches. For example, U.S. Pat. No. 6,207,734 describes the use of a cationic modified starch as a creping adhesive. Typically these adhesives are added along with release or modifying agents, such as polyvinyl alcohol and a cationic polyamide-epihalohydrin resin. Generally these compositions are added at relatively modest amounts, such as less than about 100 milligrams of creping composition per square meter dryer surface area. These low add-on levels ensure proper adhesion and release without stiffening the web or compromising other important sheet properties.

While prior art creping compositions comprising starches have been successful in balancing sheet properties and creping performance, they are limited in regards to the types of polysaccharides which may be employed and do not include prebiotics, which unlike starches, are non-digestible polysaccharides. Moreover, prior art creping compositions have generally been added in limited amounts, typically far less than the amount necessary to provide any health benefit to a consumer. Therefore there remains a need in the art for a creping composition and more specifically a prebiotic creping composition that not only successfully balances sheet properties and creping performance, but may also be added to the tissue web in a sufficient amount so as to provide a prebiotic effect.

SUMMARY OF THE DISCLOSURE

The present inventors have now discovered a creping composition comprising a prebiotic that may be used to produce creped prebiotic tissue webs and products without sacrificing important tissue properties such as strength, stiffness or softness. Generally, to prepare the inventive tissue products a creping composition comprising a prebiotic is applied to an embryonic tissue web during creping. The prebiotic composition may be applied at the creping stage by spraying the creping composition onto a rotating cylindrical dryer, such as a Yankee dryer, and transferring the creping composition to the embryonic tissue web. Preferably the creping composition is transferred in sufficient amounts to the tissue web so as to provide a prebiotic effect in use. For example, in certain embodiments the resulting creped tissue product comprises greater than about 2 mg/m$^2$ (based upon the surface area of the tissue) prebiotic. Manufacturing tissue in this manner generally results in a tissue web having physical properties comparable to or better than commercially available, non-prebiotic tissues, such as a TS7 value less than about 10. In other embodiments the creped tissue product may have a fine crepe structure, measured as % COV from 200-390 µm, from about 20 to about 25.

Accordingly, in one embodiment the present invention provides a creped tissue web comprising greater than about 2 mg prebiotic per square meter of web surface area (mg/m$^2$), wherein the tissue web has a TS7 value less than about 10.

In other embodiments the present invention provides a creped tissue web comprising greater than about 2 mg/m$^2$, the web having a basis weight greater than about 10 grams per square meter (gsm) and a bulk greater than about 3 cubic centimeters per gram (cc/g).

In still other embodiments the present invention provides a creped tissue web comprising greater than about 2 mg/m$^2$ prebiotic and from about 0.5 to about 5 mg/m$^2$ α-hydroxy acid, wherein the tissue web has a GMT greater than about 500 g/3" and a TS7 value less than about 10.

In yet other embodiments the present invention provides a multi-ply tissue product comprising at least one creped tissue ply comprising greater than about 2 mg/m$^2$ prebiotic selected from the group consisting of insulin, fructo-oligosaccharide (FOS), lactulose and galacto-oligosaccharide (GOS), the tissue product having a GMT greater than about 500 g/3" and a TS7 value less than about 10.

In other embodiments the present invention provides a method of manufacturing a prebiotic creped tissue web comprising the steps of dispersing cellulosic fibers to form a fiber slurry, forming a wet tissue web, partially dewatering the wet tissue web, applying a creping composition comprising a prebiotic selected from the group consisting of insulin, fructo-oligosaccharide (FOS), lactulose and galacto-oligosaccharide (GOS) to a creping cylinder, pressing the partially dewatered tissue web to the creping cylinder, drying the tissue web and creping the dried tissue web from the creping cylinder.

BRIEF DESCRIPTION OF DRAWINGS

FIG. 1 illustrates an apparatus for measuring fine crepe structure as described in the Test Methods section, below.

DEFINITIONS

As used herein, the terms "TS7" and "TS7 value" refer to an output of an EMTEC Tissue Softness Analyzer ("TSA") (Emtec Electronic GmbH, Leipzig, Germany) as described in the Test Methods section. The units of the TS7 are dB V$^2$ rms; however, TS7 values are often referred to herein without reference to units.

As used herein, the term "fine crepe structure" refers to the structure of crepe folds on the surface of a creped tissue web. Fine crepe structure is measured using the crepe structure test method described below. Fine crepe structure is reported as the percent coefficient-of-variation (% COV) at 200-390 µm.

As used herein, the term "Geometric Mean Tensile" (GMT) refers to the square root of the product of the machine direction tensile and the cross-machine direction tensile of the web, which are determined as described in the Test Methods section.

As used herein, the term "Slope," also referred to as "modulus," refers to slope of the line resulting from plotting tensile versus stretch and is an output of the MTS TestWorks™ in the course of determining the tensile strength as described in the Test Methods section. Slope is reported in the units of grams (g) per unit of sample width (inches) and is measured as the gradient of the least-squares line fitted to the load-corrected strain points falling between a specimen-generated force of 70 to 157 grams (0.687 to 1.540 N) divided by the specimen width.

As used herein, the term "GM Slope" generally refers to the square root of the product of the machine direction and cross-machine direction slopes, and is an output of the MTS TestWorks™ in the course of determining the tensile strength as described in the Test Methods section.

As used herein the term "Stiffness Index" refers to the quotient of the GM Slope (having units of grams) divided by the Geometric Mean Tensile (having units of grams).

As used herein, the term "tissue product" refers to products made from base webs comprising fibers and includes, bath tissues, facial tissues, paper towels, industrial wipers, foodservice wipers, napkins, medical pads, and other similar products.

As used herein, the terms "tissue web" and "tissue sheet" refer to a cellulosic web suitable for making a tissue product. Tissue webs typically have a basis weight greater than about 10 gsm and a sheet bulk greater than about 3.0 cc/g.

As used herein the term "basis weight" generally refers to the conditioned dry weight per unit area of a tissue and is generally expressed as gsm. Basis weight is measured herein using TAPPI test method T-220.

DETAILED DESCRIPTION OF THE DISCLOSURE

The present inventors have now surprisingly discovered that prebiotics may be employed as one component of a creping composition in the preparation of creped tissue products and that the prebiotics may be added at sufficiently high amounts to have a prebiotic effect in use, without negatively affecting tissue product properties, such as tensile strength, stiffness or softness. Thus, in certain embodiments the present invention provides soft, durable creped prebiotic tissue products that are able to improve the growth of healthy bacteria such as Bifidobacterium spp. or Lactobacillus spp. without promoting growth of enteropathogenic bacteria. The tissue products provide these benefits yet have suitable tissue product physical properties. For example, in certain embodiments the creped prebiotic tissue product may have a GMT greater than about 500 g/3", a Stiffness Index less than about 20 and a TS7 value less than about 10, yet provide a prebiotic effect in use. In short, the prebiotic tissue products of the present invention have physical properties comparable or improved compared to conventional tissue products but also provide a prebiotic benefit.

Prebiotic agents useful in the present invention comprise one or more saccharides (also referred to herein as carbohydrates or sugars) which are non-digestible by a human digestive system. Generally prebiotics stimulate the growth or activity of bacteria in the digestive system of a human upon administration and are beneficial to the health of the human body. In another embodiment, the prebiotic comprises one or more non-digestible saccharides where the one or more saccharides are a polysaccharide having a degree of polymerization greater than 10. In another embodiment, the prebiotic comprises a mixture of a non-digestible polysaccharide having a degree of polymerization greater than 10 and one or more digestible saccharides. Digestible saccharides are those which are digestible by a human digestive system. In one embodiment, the one or more digestible saccharides are lactose, galactose, or glucose.

Saccharides that are not digestible by humans and are useful prebiotics within the scope of the present invention include, but are not limited to, transgalactooligosaccharides, galacto-oligosaccharides, lactulose, raffinose, stachyose, lactosucrose, fructo-oligosaccharides, isomalto-oligosaccharides, xylo-oligosaccharides, paratinose oligosaccharides, difructose anhydride III, sorbitol, maltitol, lactitol, reduced paratinose, cellulose, β-glucose, β-galactose, β-fructose, verbascose, galactinol, and β-glucan, guar gum, pectin, high sodium alginate, and lambda carrageenan.

In one embodiment the prebiotic comprises a saccharide that is insulin, fructo-oligosaccharide (FOS), lactulose, galacto-oligosaccharide (GOS), raffinose, or stachyose. In a particularly preferred embodiment the prebiotic composition comprises at least one beta-glycosidic (e.g., beta galactosidic or beta glucosidic) bond or at least one alpha-glycosidic (e.g., alpha galactosidic or alpha glucosidic) bond, and is non-digestible by a human digestive system, but can be digested by a bacterium. In one embodiment the bacterium is a Bifidobacterium spp. or Lactobacillus spp.

In other embodiments the prebiotic comprises one or more fructo-oligosaccharides. Fructo-oligosaccharides are generally short-chain oligosaccharides comprised of D-fructose and D-glucose, containing from three to five monosaccharide units. Fructo-oligosaccharides are generally non-digestible and act to stimulate the growth of Bifidobacterium spp. or Lactobacillus spp.

In one particularly preferred embodiment the prebiotic comprises one or more insulins. Insulins are generally fructose-containing oligosaccharides and belong to a class of carbohydrates known as fructans. Insulins comprise fructose units in a beta-(2-I) glucosidic linkage and comprise a terminal glucose unit. The average degree of polymerization of insulins generally ranges from about 10 to 12. Insulins stimulate the growth of Bifidobacterium spp. or Lactobacillus spp.

In still other embodiments the prebiotic comprises one or more isomalto-oligosaccharides. Isomalto-oligosaccharides generally comprise a mixture of alpha-D-linked glucose oligomers including, for example, isomaltose, panose, isomaltotetraose, isomaltopentaose, nigerose, kojibiose, isopanose and higher branched oligosaccharides. Isomaltooligosaccharides generally act to stimulate the growth of Bifidobacterium spp. or Lactobacillus spp.

In other embodiments the prebiotic comprises one or more xylo-oligosaccharides. Xylo-oligosaccharides are comprised of oligosaccharides containing beta (I→4) linked xylose residues. The degree of polymerization of xylo-oligosaccharides is generally from two to four.

When added as a component of a creping composition, the prebiotic generally comprises less than about 10 percent, by weight of the creping composition, and more preferably less than about 5 percent and still more preferably less than about 2 percent, such as from about 0.1 to about 2 percent and more preferably from about 0.5 to about 1 percent, by weight of the creping composition. For example, in one embodiment the prebiotic composition comprises from about 0.5 to about 2 percent, by weight of the composition, insulin. In another embodiment the prebiotic composition comprises from about 0.5 to about 1 percent, by weight of the composition, insulin and from about 0.5 to about 1 percent, by weight of the composition, fructo-oligosaccharides.

Generally the prebiotic is added to the web such that the web comprises greater than about 2 mg of prebiotic per square meter of tissue surface area (mg/m$^2$), such as form about from about 2 to about 2,000 mg/m$^2$, such as from about 2 to about 1,000 mg/m$^2$ and still more preferably from about 2 to about 200 mg/m$^2$. At the foregoing levels of prebiotic the creped tissue web may be incorporated into a tissue product that when used by a user provides a prebiotic effect by stimulating the growth of *L. crispatus* and inhibiting the growth of *E. coli*.

In addition to a prebiotic, the compositions of the present invention may also comprise an α-hydroxy acid. Alpha-hydroxy acids useful in the present invention generally comprise mono- or polycarboxylic acids having one or more hydroxyl functional groups at least one of which is introduced into the α-position (i.e., on the carbon atom adjacent to the carboxyl functional group). Examples of particularly useful α-hydroxy acids include citric acid, lactic acid, methyllactic acid, phenyllactic acid, malic acid, mandelic acid, glycolic acid, tartronic acid, tartaric acid and gluconic acid. In particularly preferred embodiments the α-hydroxy acid is selected from the group consisting of citric acid, lactic acid, malic acid, glycolic acid and tartaric acid.

The prebiotic creping composition may comprise a single α-hydroxy acid or a combination of two or more α-hydroxy acids. For example, in one embodiment the composition comprises lactic acid and an α-hydroxy acid selected from the group consisting of citric acid, methyllactic acid, phenyllactic acid, malic acid, mandelic acid, glycolic acid, tartronic acid, tartaric acid and gluconic acid.

In those instances where the creping composition comprises an α-hydroxy acid the acid is provided in amounts sufficient to provide a synergistic prebiotic effect when administered to a user along with the prebiotic agent. Thus, α-hydroxy acid may be present in an amount sufficient to stimulate the growth of certain healthy bacteria such as *Bifidobacterium breve*, *Bifidobacterium infantis*, *Bifidobacterium longum* and *Bifidobacterium adolescentis* on one hand, and *Lactobacillus bulgaricus*, *Lactobacillus acidophilus*, *Lactobacillus gasseri*, *Lactobacillus crispatus*, *Lactobacillus casei*, *Lactobacillus plantarum*, *Streptococcus faecium*, and *Streptococcus thermophilus* on the other. Accordingly, the α-hydroxy acid may range from 0.05 to 2 percent by weight such as from about 0.1 to about 1 percent by weight and more preferably from 0.1 to 0.5 percent by weight, based on the weight of the composition.

Generally, the ratio of α-hydroxy acid to prebiotic agent ranges from about 1:50 to about 1:1,000, such as from about 1:50 to about 1:500 and more preferably from about 1:100 to about 1:200. For example, in one embodiment, the composition comprises from about 1 to about 10 percent, by weight of the composition, prebiotic agent, such as FOS, and from about 0.05 to about 1.0 percent, by weight of the composition, α-hydroxy acid, such as lactic acid. Depending on the transfer and retention of the creping composition to the tissue web, the resulting web may, in certain embodiments comprise prebiotic and α-hydroxy acid, where the ratio of α-hydroxy acid to prebiotic agent ranges from about 1:50 to about 1:1,000, such as from about 1:50 to about 1:500 and more preferably from about 1:100 to about 1:200.

Fibrous webs comprising a prebiotic composition made according to the present invention can be incorporated into multi-ply products. For instance, in one aspect, a fibrous web made according to the present invention can be attached to one or more other fibrous webs to form a wiping product having desired characteristics. The other webs laminated to the fibrous web of the present invention can be, for instance, a wet-creped web, a calendered web, an embossed web, a through-air dried web, a creped through-air dried web, an uncreped through-air dried web, an airlaid web, and the like, and may or may not comprise a prebiotic.

In one aspect, when incorporating a fibrous web made according to the present invention into a multi-ply product, it may be desirable to only apply the creping composition comprising a prebiotic to one side of the fibrous web and to thereafter crepe the treated side of the web. The creped side of the web is then used to form an exterior surface of a multi-ply product. The untreated and uncreped side of the web, on the other hand, is attached by any suitable means to one or more plies.

In those embodiments where the tissue product comprises more than one ply, it is preferred that at least one ply comprises a prebiotic creped tissue web prepared according to the invention and more preferably the creped prebiotic tissue web comprises at least about 2 mg of prebiotic per square meter of web surface area. As one skilled in the art will appreciate, the creped prebiotic tissue web may be combined with non-prebiotic containing webs and in those instances the total amount of prebiotic per square meter of tissue surface area may be less than 2 mg, yet the plies may be arranged such that the prebiotic web contacts a user in-use and provides a prebiotic effect. Generally the prebiotic effect is demonstrated by increasing the in vivo growth rate or activity of healthy bacteria, such as *Bifidobacterium* spp. or *Lactobacillus* spp. without promoting growth of, or inhibit the growth of, enteropathogenic bacteria, such as *Staphylococcus aureus*, particular strains of *Escherichia coli* (*E. coli*), or *Salmonella* spp. In a particularly preferred embodiment the tissue product comprises at least about 2 mg of prebiotic per square meter of web surface area and use of the tissue by a user stimulates the growth of *L. crispatus* and inhibiting the growth of *E. coli*.

Not only do the inventive tissues provide a prebiotic effect, but surprisingly the products have comparable or better physical properties than commercially available tissues. Despite the addition of prebiotic, even at relatively high add-on levels such as greater than about 100 mg/m$^2$, during creping of the tissue, the prebiotic tissue products are soft, strong and have relatively low stiffness.

TABLE 1

| Sample | GMT (g/3") | GMM (kg) | Stiffness Index | TS7 |
|---|---|---|---|---|
| Kleenex ® Mainline Facial Tissue | 772 | 9.93 | 12.9 | 9.85 |
| Puffs Basic ® Facial Tissue | 689 | 8.28 | 12.0 | 10.62 |
| Puffs Plus ® Facial Tissue | 851 | 12.22 | 14.4 | — |
| Puffs Ultra Strong and Soft ® Facial Tissue | 954 | 10.51 | 11.0 | — |
| Publix ® Facial Tissue | 741 | 10.75 | 14.5 | 12.0 |
| Up&Up ™ Everyday Facial Tissue | 814 | 10.59 | 13.0 | 11.4 |
| Scotties ® 2-Ply Facial Tissue | 816 | 14.82 | 18.2 | 12.6 |
| Inventive Facial Tissue | 980 | 15.71 | 16.0 | 8.28 |

Accordingly, tissue products prepared according to the present invention generally have a geometric mean tensile strength (GMT) greater than about 500 g/3", such as from about 500 to about 1,000 g/3", and more preferably from about 700 to about 900 g/3". At these tensile strengths the tissue products are preferably not overly stiff as a result of the addition of the prebiotic agent. Stiffness may be measured as a reduction in the slope of the tensile-strain curve (measured as GM Slope) or the Stiffness Index at a given tensile strength. For example, tissue products as described herein generally have a GM Slope less than about 20 kgf, such as from about 10 to about 20 kgf and more preferably from about 12 to about 18 kgf. The GM Slopes are achieved at relatively modest tensile strengths, such as a GMT from about 700 to about 1,000 g/3", yielding Stiffness Indexes less than about 20 and more preferably less than about 18, such as from about 14 to about 18.

In addition to the foregoing tensile strengths and moduli, the products preferably have an MD Stretch from greater than about 8 percent and more preferably greater than about 10 percent, such as from about 10 to about 15 percent. The tissue products may also have a CD stretch greater than about 5 percent, such as from about 5 to about 10 percent.

Generally the tissue webs of the present invention have a basis weight of at least about 10 gsm, such as from about 10 to about 25 gsm and sheet bulk greater than 3 cc/g, such as from about 3 to about 8 cc/g. The tissue webs may be converted into tissue products having basis weights from about 25 gsm and more preferably at least about 30 gsm, such as from about 30 to about 45 gsm. At these basis weights the tissue products of the present invention have a GMT less than about 1,000 g/3", such as from about 500 top about 1,000 g/3". In one particularly preferred embodiment the present invention provides a creped tissue product comprising at least one tissue ply having a prebiotic agent disposed thereon, the prebiotic selected from the group consisting of insulin, fructo-oligosaccharide (FOS), lactulose, galacto-oligosaccharide (GOS), raffinose, stachyose, isomalto-oligosaccharide, and xylo-oligosaccharide, the tissue product having a basis weight from about 30 to about 45 gsm, a GMT from about 500 to about 1,000 g/3" and a Stiffness Index less than about 20.

In addition to having suitable tensile properties, tissue webs and products prepared according to the present invention surprisingly have excellent softness and fine crepe structure. For example, tissue webs prepared according to the present invention generally have a tissue softness value (also referred to herein as a "TS7 value"), measured using EMTEC Tissue Softness Analyzer ("TSA") (Emtec Electronic GmbH, Leipzig, Germany) as described in the Test Methods section, less than about 10.0, such as from about 8.0 to about 10.0. Accordingly, in one embodiment the present invention provides a creped tissue product comprising at least one tissue ply, the tissue ply comprising at least about 100 mg of prebiotic per square meter of tissue, the tissue product having a GMT from about 500 to about 1,000 g/3" and a TS7 value from about 8.0 to about 10.0.

In other embodiments tissue webs and products prepared according to the present invention have a fine crepe structure. In certain embodiments the present invention provides a tissue web having a fine crepe structure less than 25% COV, measured at a wavelength from 200-390 μm, such as from about 20 to about 25% COV and more preferably from about 21 to about 23% COV. Thus, in one embodiment the present invention provides a creped tissue web comprising at least about 100 mg of prebiotic per square meter of tissue web, the tissue web having a fine crepe structure from about 20 to about 25% COV, measured at a wavelength from 200-390 μm.

In general, any suitable fibrous web may be treated in accordance with the present invention. For example, in one aspect, the base sheet can be a tissue product, such as a bath tissue, a facial tissue, a paper towel, a napkin, and the like. Fibrous products can be made from any suitable types of fiber. Fibrous products made according to the present invention may include single-ply fibrous products or multi-ply fibrous products. For instance, in some aspects, the product may include two plies, three plies, or more.

Fibers suitable for making fibrous webs comprise any natural or synthetic fibers including both nonwoody fibers and woody or pulp fibers. Pulp fibers can be prepared in high-yield or low-yield forms and can be pulped in any known method, including kraft, sulfite, high-yield pulping methods and other known pulping methods. Fibers prepared from organosolv pulping methods can also be used, including the fibers and methods disclosed in U.S. Pat. Nos. 4,793,898, 4,594,130, and 3,585,104. Useful fibers can also be produced by anthraquinone pulping, exemplified by U.S. Pat. No. 5,595,628.

The fibrous webs of the present invention can also include synthetic fibers. For instance, the fibrous webs can include up to about 10 percent, such as up to about 30 percent or up to about 50 percent or up to about 70 percent or more by dry weight, to provide improved benefits. Suitable synthetic fibers include rayon, polyolefin fibers, polyester fibers, bicomponent sheath-core fibers, multi-component binder fibers, and the like. Synthetic cellulose fiber types include rayon in all its varieties and other fibers derived from viscose or chemically-modified cellulose.

Chemically treated natural cellulosic fibers can be used, for example, mercerized pulps, chemically stiffened or crosslinked fibers, or sulfonated fibers. For good mechanical properties in using web forming fibers, it can be desirable that the fibers be relatively undamaged and largely unrefined or only lightly refined. While recycled fibers can be used, virgin fibers are generally useful for their mechanical properties and lack of contaminants. Mercerized fibers, regenerated cellulosic fibers, cellulose produced by microbes, rayon, and other cellulosic material or cellulosic derivatives can be used. Suitable web forming fibers can also include recycled fibers, virgin fibers, or mixes thereof.

In general, any process capable of forming a web can also be utilized in the present invention. For example, a web forming process of the present invention can utilize creping, wet creping, double creping, recreping, double recreping, embossing, wet pressing, air pressing, through-air drying, hydroentangling, creped through-air drying, co-forming, air-laying, as well as other processes known in the art. For hydroentangled material, the percentage of pulp is about 70 to 85 percent.

Fibrous webs that may be treated in accordance with the present invention may include a single homogenous layer of fibers or may include a stratified or layered construction. For instance, the fibrous web ply may include two or three layers of fibers. Each layer may have a different fiber composition. For example a three-layered headbox generally includes an upper headbox wall and a lower headbox wall. Headbox further includes a first divider and a second divider, which separate three fiber stock layers.

Each of the fiber layers comprises a dilute aqueous suspension of papermaking fibers. The particular fibers contained in each layer generally depend upon the product being formed and the desired results. For instance, the fiber composition of each layer may vary depending upon whether a bath tissue product, facial tissue product or paper towel product is being produced. In one aspect, for instance, the middle layer contains southern softwood kraft fibers either alone or in combination with other fibers such as high yield fibers. Outer layers, on the other hand, contain softwood fibers, such as northern softwood kraft. In an alternative aspect, the middle layer may contain softwood fibers for strength, while the outer layers may comprise hardwood fibers, such as *eucalyptus* fibers, for a perceived softness.

In general, any process capable of forming a base sheet may be utilized in the present invention. For example, an endless traveling forming fabric, suitably supported and driven by rolls, receives the layered papermaking stock issuing from the headbox. Once retained on the fabric, the layered fiber suspension passes water through the fabric. Water removal is achieved by combinations of gravity, centrifugal force and vacuum suction depending on the forming configuration. Forming multi-layered paper webs is also described and disclosed in U.S. Pat. No. 5,129,988, which is incorporated herein by reference in a manner that is consistent herewith.

Preferably the formed web is dried by transfer to the surface of a rotatable heated dryer drum, such as a Yankee dryer. In accordance with the present invention, the creping composition may be applied topically to the tissue web while the web is traveling on the fabric or may be applied to the surface of the dryer drum for transfer onto one side of the tissue web. In this manner, the creping composition is used to adhere the tissue web to the dryer drum. In this embodiment, as the web is carried through a portion of the rotational path of the dryer surface, heat is imparted to the web causing most of the moisture contained within the web to be evaporated. The web is then removed from the dryer drum by a creping blade. Creping the web, as it is formed, further reduces internal bonding within the web and increases softness. Applying the creping composition to the web during creping, on the other hand, may increase the strength of the web.

In another embodiment the formed web is transferred to the surface of the rotatable heated dryer drum, which may be a Yankee dryer. The press roll may, in one embodiment, comprise a suction pressure roll. In order to adhere the web to the surface of the dryer drum, a creping adhesive may be applied to the surface of the dryer drum by a spraying device. The spraying device may emit a creping composition made in accordance with the present invention or may emit a conventional creping adhesive. The web is adhered to the surface of the dryer drum and then creped from the drum using the creping blade. If desired, the dryer drum may be associated with a hood. The hood may be used to force air against or through the web.

In other embodiments, once creped from the dryer drum, the web may be adhered to a second dryer drum. The second dryer drum may comprise, for instance, a heated drum surrounded by a hood. The drum may be heated from about 25° C. to about 200° C., such as from about 100° C. to about 150° C.

In order to adhere the web to the second dryer drum, a second spray device may emit an adhesive onto the surface of the dryer drum. In accordance with the present invention, for instance, the second spray device may emit a creping composition as described above. The creping composition not only assists in adhering the tissue web to the dryer drum, but also is transferred to the surface of the web as the web is creped from the dryer drum by the creping blade. Once creped from the second dryer drum, the web may, optionally, be fed around a cooling reel drum and cooled prior to being wound on a reel.

It has now been discovered that the prebiotic composition may itself be used as a creping composition to adhere the web to a heated drum or may be included as one component of a conventional creping composition. In both instances, whether applied as an additional component of a conventional creping composition or alone, addition of a prebiotic composition at the creping stage of tissue manufacture has proven to be an effective means of applying the prebiotic composition to the surface of a web without negatively affecting other important web properties.

Thus, in certain embodiments the present invention provides a creping composition comprising a prebiotic and a creping adhesive. Creping adhesives are well known in the art and may include for example, polyvinyl alcohol, ethylene/vinyl acetate copolymer, animal glue, polyamidoamine-epichlorohydrin resins (PAE resins) and polyvinyl acetate. In particularly preferred embodiments the creping composition comprises a prebiotic and one or more cationic polyamidoamine-epichlorohydrin resins, such as those commercially available under the tradenames Crepetrol™ and Rezosol™ (Ashland Water Technologies, Wilmington, Del.).

In other embodiments, in addition to a prebiotic and a creping adhesive, the creping composition may also include a creping release aid, such as those commercially available under the trade name Busperse® (Buckman Laboratories, Memphis, Tenn.). Suitable release aids include aliphatic polyols or oligomers thereof having a number average molecular weight of less than 600, polyalkanolamines, aromatic sulfonamides, pyrrolidone, and mixtures thereof. Other release aids are propylene glycol, diethylene glycol, glycerol, triethylene glycol, dipropylene glycol, polyalkanolamines, aromatic sulfonamides, pyrrolidone, and mixtures thereof. In those embodiments where a release aid is used, ethylene glycol is particularly preferred.

In other embodiments the creping composition comprises a thermoplastic resin, such as the composition disclosed in U.S. Pat. No. 7,807,023, which is incorporated herein in a manner consistent with the present invention. The thermoplastic resin may be contained, for instance, in an aqueous dispersion prior to application to the creping surface. In one particular embodiment, the creping composition may comprise a non-fibrous olefin polymer. The creping composition, for instance, may comprise a film-forming composition and the olefin polymer may comprise a copolymer of ethylene and at least one comonomer comprising an alkene, such as 1 octene. The creping composition may also contain a dispersing agent, such as a carboxylic acid. Examples of particular dispersing agents, for instance, include fatty acids, such as oleic acid or stearic acid.

The creping compositions of the present invention are typically transferred to the web at high levels, such that at least about 30 percent of the creping composition applied to the Yankee is transferred to the web, more preferably at least about 45 percent is transferred and still more preferably at least about 60 percent is transferred. Generally from about 45 to about 65 percent of the creping composition applied to the Yankee dryer is transferred to the web. Thus, the amount of creping additive transferred to the sheet is a function of the amount of creping additive applied to the Yankee dryer.

The total amount of creping composition applied to the web can be in the range of from about 0.01 to about 10 percent by weight, based upon the total weight of the web, such as from about 0.1 to about 5 percent by weight, such as from about 0.5 to about 3 percent by weight. To achieve the desired additive application levels the add on rate of creping composition to the dryer, measured as mass (i.e., mg) per unit area of dryer surface (i.e., $m^2$), may range from about 5 to about 2,000 $mg/m^2$, and still more preferably from about 10 to about 1,000 $mg/m^2$, such as from about 20 to about 500 $mg/m^2$. In a particularly preferred embodiment the creping composition comprises a polyamine-epichlorohydrin resin, a prebiotic and an α-hydroxy acid, which is applied to the Yankee drier at levels from about 5 to about 100 $mg/m^2$.

At the foregoing add-on levels creped tissue products of the present invention generally comprise greater than about 2 mg of prebiotic per square meter of tissue surface area, such as form about from about 2 to about 1,000 $mg/m^2$ and more preferably from about 2 to about 100 $mg/m^2$. In addition to a prebiotic, the creped tissue products may also comprise from about 0.1 mg α-hydroxy acid per square meter of tissue product, such as from about 0.1 to about 10 $mg/m^2$. Generally the creping composition is disposed on the surface of the tissue web, although a portion of the composition may permeate the web. Thus, in one embodiment the present invention provides a creped tissue web having a first and a second side, wherein the first side contacts a cylindrical dryer during manufacture, the first side having a creping composition comprising a prebiotic and optionally an α-hydroxy acid disposed thereon.

In addition to applying the creping composition during formation of the fibrous web, the prebiotic creping composition of the present invention may also be used in post-forming processes. For example, in one aspect, the prebiotic creping composition may be used during a print-creping process. Specifically, once topically applied to a fibrous web, the creping composition has been found well-suited to adhering the fibrous web to a creping surface, such as in a print-creping operation.

For example, once a fibrous web is formed and dried the prebiotic creping composition may be applied to at least one side of the web and the at least one side of the web may then be creped. In general, the creping composition may be applied to only one side of the web and only one side of the web may be creped, the creping composition may be applied to both sides of the web and only one side of the web is creped, or the creping composition may be applied to each side of the web and each side of the web may be creped.

In one embodiment the prebiotic creping composition may be added to one side of the web by creping, using either an in-line or off-line process. A tissue web is passed through a first creping composition application station that includes a nip formed by a smooth rubber press roll and a patterned rotogravure roll. The rotogravure roll is in communication with a reservoir containing a first creping composition. The rotogravure roll applies the creping composition to one side of the web in a preselected pattern. The web is then contacted with a heated roll, which can be heated to a temperature, for instance, up to about 200° C., and more preferably from about 100° C. to about 150° C. In general, the web can be heated to a temperature sufficient to dry the web and evaporate any water. It should be understood, that besides the heated roll, any suitable heating device can be used to dry the web. For example, in an alternative embodiment, the web can be placed in communication with an infra-red heater in order to dry the web. Besides using a heated roll or an infra-red heater, other heating devices can include, for instance, any suitable convective oven or microwave oven.

From the heated roll, the web can be advanced by pull rolls to a second creping composition application station, which includes a transfer roll in contact with a rotogravure roll, which is in communication with a reservoir containing a second creping composition. The second creping composition may be applied to the opposite side of the web in a preselected pattern. The first and second creping compositions may contain the same ingredients or may contain different ingredients. Alternatively, the creping compositions may contain the same ingredients in different amounts as desired. Once the second creping composition is applied the web is adhered to a creping roll by a press roll and carried on the surface of the creping drum for a distance and then removed therefrom by the action of a creping blade. The creping blade performs a controlled pattern creping operation on the second side of the tissue web. Although the creping composition is being applied to each side of the tissue web, only one side of the web undergoes a creping process. It should be understood, however, that in other embodiments both sides of the web may be creped.

Once creped the tissue web may be pulled through a drying station. The drying station can include any form of heating unit, such as an oven energized by infra-red heat, microwave energy, hot air, or the like. A drying station may be necessary in some applications to dry the web and/or cure the creping composition. Depending upon the creping composition selected, however, in other applications a drying station may not be needed.

Test Methods

Tensile

Samples for tensile strength testing are prepared by cutting a 3 inches (76.2 mm) by 5 inches (127 mm) long strip in either the machine direction (MD) or cross-machine direction (CD) orientation using a JDC Precision Sample Cutter (Thwing-Albert Instrument Company, Philadelphia, Pa., Model No. JDC 3-10, Ser. No. 37333). The instrument used for measuring tensile strengths is an MTS Systems Sintech 11S, Serial No. 6233. The data acquisition software is MTS TestWork™ for Windows Ver. 4 (MTS Systems Corp., Research Triangle Park, N.C.). The load cell is selected from either a 50 Newton or 100 Newton maximum, depending on the strength of the sample being tested, such that the majority of peak load values fall between 10 and 90 percent of the load cell's full scale value. The gauge length between jaws is 4±0.04 inches. The jaws are operated using pneumatic-action and are rubber coated. The minimum grip face width is 3 inches (76.2 mm), and the approximate height of a jaw is 0.5 inches (12.7 mm). The crosshead speed is 10±0.4 inches/min (254±1 mm/min), and the break sensitivity is set at 65 percent. The sample is placed in the jaws of the instrument, centered both vertically and horizontally. The test is then started and ends when the specimen breaks. The peak load is recorded as either the "MD tensile strength" or the "CD tensile strength" of the specimen depending on the sample being tested. At least six (6) representative specimens are tested for each product, taken "as is," and the arithmetic average of all individual specimen tests is either the MD or CD tensile strength for the product.

Caliper

Caliper is measured in accordance with TAPPI test method T411 om-89 "Thickness (caliper) of Paper, Paperboard, and Combined Board" with modifications to the size of the pressure foot and the amount of pressure applied to the sample. In particular, the micrometer used for carrying out the caliper measurement is an Emveco 200-A Electronic Microgage available from Emveco, Inc., Newberg, Oreg., having a circular pressure foot area of 2500 square millimeters and a diameter of 56.42 millimeters. The dwell time is 3 seconds, the lowering rate is 0.8 millimeters per second and the applied pressure is 2 kilo-Pascals. Caliper may be used to calculate sheet bulk, which is the basis weight divided by caliper. The resulting sheet bulk is expressed in cubic centimeters per gram (cc/g).

Tissue Softness (TSA)

Sample softness was analyzed using an EMTEC Tissue Softness Analyzer ("TSA") (Emtec Electronic GmbH, Leipzig, Germany). The TSA comprises a rotor with vertical blades which rotate on the test piece applying a defined contact pressure. Contact between the vertical blades and the test piece creates vibrations, which are sensed by a vibration sensor. The sensor then transmits a signal to a PC for processing and display. The signal is displayed as a frequency spectrum. The frequency analysis in the range of approximately 200 to 1000 Hz represents the surface smoothness or texture of the test piece. A high amplitude peak correlates to a rougher surface. A further peak in the frequency range between 6 and 7 kHz represents the softness of the test piece. The peak in the frequency range between 6 and 7 kHz is herein referred to as the TS7 Softness Value and is expressed as dB V2 rms. The lower the amplitude of the peak occurring between 6 and 7 kHz, the softer the test piece.

Test samples were prepared by cutting a circular sample having a diameter of 112.8 mm. All samples were allowed to equilibrate at TAPPI standard temperature and humidity conditions for at least 24-hours prior to completing the TSA testing. Only one ply of tissue is tested. Multi-ply samples are separated into individual plies for testing. The sample is placed in the TSA with the softer (dryer or Yankee) side of the sample facing upward. The sample is secured and the TS7 Softness Values measurements are started via the PC. The PC records, processes and stores all of the data according to standard TSA protocol. The reported TS7 Softness Value is the average of 5 replicates, each one with a new sample.

Fine Crepe Structure

Wrinkle-free tissues specimens are cut to 2×3 inches, such that the machine direction runs parallel with the longer dimension. Samples are used as-is, that is one-ply samples are sampled as a single ply, while two-ply samples are sampled as two plies. Cut samples are mounted on a 10×12-inch glass plate by adhering with SCOTCH® tape, or equivalent, at their corners and along their sides. Each sample is "painted" with a 50:50 mixture of PENTEL® Correction Pen fluid and n-butanol, using a top quality camel's hair brush and applying in one direction parallel to the machine direction. This preparation will reduce light reflection and refraction.

Referring to the schematic representation of the image acquisition apparatus shown in FIG. 1 below, a specimen is illuminated in a darkened room with a collimated light source produced by a slide projector or similar device. The projector used was a Kodak Ektagraphic slide projector (Model B-2) 128 having a lens 130. The projector 128 was connected to a Variable Auto-transformer, type 3PN1010, which was purchased from Staco Energy Products, Co. having an office in Dayton, Ohio. The auto-transformer is used to adjust the projector's illumination level. The projector 128, with its attached lens 130, was mounted on a support 132. In turn, the support was attached to a base 134. The collimated light source was adjusted to hit the top surface of the tissue specimen 122 at an angle of 20 degrees. The prepared tissue sample 122 is positioned flat on top of the auto-stage 146 with the crepe pattern aligned orthogonal with respect to the light source, resulting in shadows cast by any crepe folds. The reflected light is viewed and an image acquired by a Leica Microsystems DFC-310 camera operated in monochrome mode 136 having a 40-mm El-Nikkor lens (f-stop=4) 138 with a 20-mm extension tube 140 to generate a 1024×1024 pixel gray-scale image.

The DFC-310 video camera 136 was mounted on a Polaroid MP-4 Land Camera (Polaroid Resource Center, Cambridge, Miss.) standard support 142. The support was attached to a KREONITE macro-viewer 144 available from Kreonite, Inc., having an office in Wichita, Kans. An auto-stage, Prior Model H112/25T, 146 was placed on the upper surface of the KREONITE macro-viewer. The auto-stage 146 is a motorized apparatus known to those skilled in the analytical arts which was purchased from Prior Scientific, Inc., having an office in Rockland, Mass. The auto stage 146 was used to move the sample 122 in order to obtain six separate and distinct, non-overlapping images from the approximately 3×2-inch size specimen. The glass plates 124 with painted tissue are placed on the auto macro-stage of a Leica Microsystems QWIN Pro Image Analysis system, under the optical axis of a 40 mm El-Nikkor lens 138 with a 20-mm extension tube 140. The sample is illuminated with a slide projector to form shadows.

Referring again to FIG. 1, the distance D1 represents the distance between the upper surface of the sample and the bottom of the lens. The distance D1 was set to be approximately 7 cm. The distance D2 represents the vertical distance between the lens attached to the slide projector and the upper surface of the sample. The distance D2 was set at 23 cm. The sample was illuminated by the slide projector. The distance D3 represents the horizontal distance between a vertical line extending to the center of the video camera lens and a vertical line extending to the center of the slide projector lens. The distance D3 was set at 65 cm. These dimensions, combined with the video camera set-up, resulted in a field-of-view size of the sample surface to be approximately 8.8 mm by 8.8 mm.

The image analysis system used to acquire images was a QWIN Pro (v. 3.5.1) available from Leica Microsystems (Heerbrugg, Switzerland). A custom image acquisition program used to acquire and process gray-scale monochrome images using Quantimet User Interactive Programming System (QUIPS) language:

CONDITIONS: DFC 310 FX; 40 mm El-Nikkor lens (f/4) and 20 mm ext. tube; Projected, collimated light @ 20 deg. angle; 50/50 PENTEL/n-Butanol coating on samples; mounted on ¼" glass plate.
    INITIALIZE VARIABLES
    CALVALUE = 8.57
    IMAGE = 0
    ACQOUTPUT = 1
    SET-UP AND CALIBRATION
    Configure  (Image Store 1024 × 1024, Grey Images 45, Binaries 24)
    Clear Accepts
    Image frame  ( x 0, y 0, Width 1024, Height 1024 )
    Measure frame  ( x 30, y 150, Width 934, Height 700 )
    PauseText  ("Enter image file prefix name.")

```
    Input    (TITLE$)
    PauseText ("Position Sample and use Polaroid 803 reference to adjust white level to 0.5.")
    Image Setup DC Twain [PAUSE] (Camera 1, AutoExposure Off, Gain 0.00, ExposureTime
78.43 msec, Brightness 0, Lamp 49.99)
    Calibrate    (CALVALUE CALUNITS$ per pixel)
    For   (SAMPLE = 1 to 3, step 1)
ROUTINE TO STABILIZE LIGHT LEVEL
    Y = 0
    Z = 0
    SP = 0
    SIB = 0
    P = 0
    MGREYIMAGE = 0
    MGREYMASK = 0
    FIELDS = 1000
    TWICE = 0
    Correlation GL Value for top 1% px Method, and DFC 310 FX = 187
    For   (LIGHT = 1 to 30, step 1)
      Image Setup DC Twain [PAUSE] (Camera 1, AutoExposure Off, Gain 0.00,
      ExposureTime 78.43 msec, Brightness 0, Lamp 49.99)
      Acquire    (into Image0)
      Graphics   (Inverted Grid, 1 × 1 Lines, Grid Size 930 × 693, Origin 30 × 151,
      Thickness 5, Orientation 0.000000, to Binary0)
      Image frame    ( x 0, y 0, Width 1024, Height 1024)
      Measure frame    ( x 30, y 150, Width 934, Height 700)
      Measure Grey    ( plane MGREYIMAGE, mask MGREYMASK,
    histogram into GREYHIST(256), stats into GREYSTATS(3) )
    Selected parameters: Pixels, MeanGrey, Std Dev
       A = GREYSTATS(2)
       B = GREYSTATS(3)
       D = A+B
       For    ( X = 129 to 256, step 1 )
        Y = Y+(X*GREYHIST(X))
        Z = Z+GREYHIST(X)
      Next    ( X )
      R = Y/Z
      TP = GREYSTATS(1)
      ONEPCTPX = .01 * TP
      For    ( X = 256 to 1, step -1 )
       If ( ONEPCTPX > SP )
         P = GREYHIST(X)
         SP = SP + P
         SIB = SIB + (X * P)
         If    ( ONEPCTPX < SP )
           X = 1
      Endif
      Endif
      Next    ( X )
      AVEGL = SIB / SP
      E = AVEGL
      Display    ( E, field width: 8, left justified, 1 digit after '.', no tab follows)
      If    ( E<194 )
      If    ( E>190 )
      TWICE = TWICE+1
      If    ( TWICE=2 )
      Goto    CONTINUE
      Endif
      Endif
      Endif
      Y = 0
      Z = 0
      SP = 0
      SIB = 0
      Display    ( Image0 (on), frames (on,on), planes (off,off,off,off,off,off), lut 0, x 0, y 49, z 1,
Reduction off)
       Next    ( LIGHT )
    END LIGHT STABILIZER ROUTINE
    CONTINUE:
    STAGE SCAN PARAMETERS
    Stage    ( Define Origin )
    Stage    ( Scan Pattern, 1 × 6 fields, size 13400.150391 × 6100.000000 )
    IMAGE ACQUISITION AND DETECTION
    For    ( FIELD = 1 to 6, step 1 )
    IMAGE = IMAGE+1
    Image Setup DC Twain ( Camera 1, AutoExposure Off, Gain 0.00, ExposureTime
    Acquire    ( into Image0 )
    Grey Transform    ( WSmooth from Image0 to Image1, cycles 2, operator Horiz )
    The following line is the computer location where the acquired images are saved
    ACQFILE$ = "C:\Images\65104 - Busch\"+TITLE$+"_"+STR$(IMAGE)+".TIF"
```

```
Write image    ( from ACQOUTPUT into file ACQFILE$ )
Image frame    ( x 0, y 0, Width 1024, Height 1024 )
Stage    ( Step, Wait until stopped + 550 msecs )
Next    ( FIELD )
PauseText    ( "Position Plate to Analyze Next Tissue and click 'Continue.'")
Image Setup DC Twain [PAUSE] ( Camera 1, AutoExposure Off, Gain 0.00, ExposureTime
78.43 msec, Brightness 0, Lamp 49.99 )
Next    ( SAMPLE )
END
```

Prior to acquiring the first sample images, shading correction was performed using the QWIN software and a white 803 Polaroid film positive (or equivalent white material) covered with an opaque, translucent film. Alternatively, other non-glossy white films or sheets could be used. The system and images were also accurately calibrated using the QWIN software and a standard ruler with metric markings. The calibration was performed in the horizontal dimension of the video camera image.

After calibrating, a custom image acquisition program was executed via the QWIN software and this initially prompts the analyst to place the sample specimen within the field-of-view of the video camera. After positioning the specimen so the machine direction is parallel to the light source and the specimen is properly aligned for auto-stage motion, the analyst will then be prompted to adjust the light level setting (via the variable auto-transformer) to register between Gray-Level readings of 190-194. During this process of light adjustment, the algorithm OSC Tissue—1 will automatically display the current Gray-Level value on the video screen. After the light has been properly adjusted, the custom image acquisition acquires six images for a single tissue specimen.

Using the set-up described above, an image representing an 8.8 mm×8.8 mm field of view was generated and saved as a *.tif image file. Typically, 3 tissue specimens were selected per sample code and 6 images generated per tissue specimen resulting in 18 images generated per sample or code.

A custom Matlab software algorithm is used for this analysis. The algorithm is shown below.

```
% OSC Matlab FFT Filter_1
% Condtions: Uses gray-scale images generated from
% DGB, 11/6/2013
% EXCEL Output header
hdr={'Image','50-100um','100-200um','200-390um',
'390-790um','790-1580um'}
data(1,:)=[hdr];
% get the images
[fn,pn]=uigetfile('C:\Matlab\Images\Zhe - OSC Matlab
Method\*.*','Pick your images','MultiSelect','on');
  for j=1:length(fn),
  %% Read in image
  fnimg=([pn fn{j}]);
  a=imread(fnimg);
  figure(1);clf;imshow(a);title('Original Image');
  %% Create distance map for filtering
  sz=size(a);bw=zeros(sz);half=floor(sz/2)+1;bw(half(1),half(2))=1;
  D=bwdist(bw);
  figure(1);clf;imagesc(D);axis equal off;colorbar;title('Distance Map');
  %% Fourier Transform
  % fourier
  fa=fftshift(fft2(a));   % shift to put DC component at center
  pa=fa.*conj(fa);        % power spectrum
  % hard to see anything in raw power, so log transform it
  figure(1);clf;imagesc(log(1+pa));axis equal off;
  %% Sweep Frequency Range
  freqRng=[87 172;
     46 87;
     23 46;
     12 23;
     7 12];
  clear mn sd cover;
  for i=1:size(freqRng,1),
    % filter
    % -- note: unless you have DC signal back in, all the
    % values are centered around zero. This is done by
    % keeping the very center of the image (bw).
    fa1=fa.*(D>=freqRng(i,1) & D<freqRng(i,2) | bw);
    % convert back to real space
    ra1=ifft2(ifftshift(fa1));
    % in this example the values were real, but I suspect in
    % general there will be a small complex component
    ra1=real(ra1);
    mn(i)=mean(ra1(:));
    sd(i)=std(ra1(:));
    covar(i)=sd/mn;
    figure(1);clf;set(gcf,'color','w');
    subplot(1,3,1:2),imagesc(ra1);axis equal off;
    subplot(1,3,3),hist(ra1(:));
    xlabel('Value');ylabel('Frequency [#]');
    ttl=sprintf('Mean: %.2f, Stdv: %.2f, COV: %.2f',mn,sd,covar);
    title(ttl);
    snapnow;
  end;
  %% Output
  data(j+1,:)=[{fnimg} num2cell([covar(:)'*100])];
  %data=[{fnimg} num2cell([covar(:)'*100])];
  end;
  xlswrite('C:\Matlab\data\fft_output.xls',data);
```

Images were analyzed by running the algorithm in Matlab algorithm. The analyst is initially prompted to select the images located in the designated directory folder on the computer. After images are selected, the algorithm then processes each image and places the resulting data into an EXCEL spreadsheet located in a designated directory folder on the computer. The 200-390 μm range data set has been used to compare and contrast the surface the crepe structure of different tissues.

Prebiotic Effect Protocol

To determine whether a composition has the desired prebiotic effect, the effect of a given composition on the ratio of *L. crispatus* to *E. coli* is measured using the following protocol. *Lactobacillus crispatus* (ATCC 33820) is inoculated in Lactobacilli MRS broth and incubated without stirring or shaking and anaerobically at 37° C. *Escherichia coli* K12 (ATCC 29425) is inoculated in Tryptic Soy Broth (TSB) with shaking and aerobically at 37° C.

After overnight incubation the *L. crispatus* is washed twice and re-suspended in PBS and centrifuged at 1,000×g for 3 minutes. Washed cells are diluted 1:10 in PBS to a target of $10^6$ CFU/mL inoculum. After overnight incubation the *E. coli* is washed twice and re-suspended in PBS and centrifuged at 4,000×g for 5 minutes. Washed cells are diluted in a series of 1:10 dilutions in PBS to a target of $10^3$ CFU/mL inoculum.

The extract of dry tissue samples are prepared by placing 10 tissues into a 60-mL syringe with 10 mL PBS. The extract is then filter-sterilized and retained for analysis. Wet or moist wipe samples are prepared by expressing the fluid off the basesheet. The expressed fluid is filter-sterilized and retained for analysis. Approximately 4.5 mL of dry bath tissue extract or 4.5 mL of fluid expressed from moist wipes is added to 14-mL culture tubes (n=3). A positive control is prepared by adding 0.5 mL LAPTgGFree+1% insulin to 14-mL culture tubes (n=3). A negative control is prepared by adding 0.5 mL LAPTgGFree to 14-mL culture tubes (n=3).

One-hundred microliters of L. crispatus and E. coli inocula are added to the samples and vortexed to mix. The samples are then incubated anaerobically at 37° C. for 24 hours. Samples are then diluted in sterile PBS and plated in duplicate on Lactobacilli MRS agar to enumerate L. crispatus colonies and TSA plates to enumerate E. coli colonies. Lactobacilli MRS agar plates are incubated anaerobically, and TSA plates are incubated aerobically, at 37° C. for 24 hours. Lactobacilli MRS agar plates are evaluated to determine the viable L. crispatus counts and TSA agar plates are evaluated to determine the viable E. coli counts. Based upon the counts the $LOG_{10}$ CFU/sample is calculated for each organism for each code.

EXAMPLES

Inventive sample codes were made using a wet pressed process utilizing a conventional wet pressed pilot scale tissue machine. The sample codes had a target basis weight of about 16.3 gsm. Initially, northern softwood kraft (NSWK) pulp was dispersed in a pulper for 30 minutes at 4 percent consistency at about 100° F. The NSWK pulp was then transferred to a dump chest and subsequently diluted to approximately 3 percent consistency. The NSWK pulp was refined for 8 minutes at about 1 HP-days/MT. The NSWK fibers were added to the middle layer in the 3-layer tissue structure such that NSWK fiber contributed approximately 30 percent of the final sheet weight.

Eucalyptus hardwood kraft (EHWK) pulp was dispersed in a pulper for 30 minutes at about 4 percent consistency at about 100° F. The EHWK pulp was then transferred to a dump chest and diluted to about 3 percent consistency. The EHWK pulp fibers were added to dryer and felt layers such that EHWK pulp fibers contributed approximately 70 percent of the final sheet weight.

The wet sheet, about 10 to 20 percent consistency, was adhered to a Yankee dryer through a nip via a pressure roll. The consistency of the wet sheet after the pressure roll nip (post-pressure roll consistency or PPRC) was approximately 40 percent. The wet sheet is adhered to the Yankee dryer due to the creping composition that is applied to the dryer surface. A spray boom situated underneath the Yankee dryer sprayed the creping composition onto the dryer surface. Insulin (BENEO Orafti® HIS, available from BENEO GmbH, Mannheim, Germany) was prepared by dissolving 3071 grams in 60 liters of water (51.2 g Insulin/L). The release agent comprised Crepetrol 874 (Ashland Water Technologies, Wilmington, Del.), which was prepared by dissolving 18.54 g of Crepetrol 874 in 60 liters of water (0.31 g Crepetrol/L). When applied to the Yankee, insulin was added at about 900 gsm of dryer surface area and Crepetrol 874 was applied at 5.14 mg per square meter of dryer surface area.

The sheet was dried to about 98 to 99 percent consistency as it traveled on the Yankee dryer and to the creping blade. The creping blade subsequently scraped the tissue sheet and a portion of the creping composition off the Yankee dryer. The creped tissue basesheet was then wound onto a core traveling at about 1575 fpm (480 mpm) into soft rolls for converting.

The ability of the foregoing tissue sample to stimulate the growth of L. crispatus and inhibit the growth of E. coli was assessed using the prebiotic assay described above. Various control samples were also prepared and assessed, as well as a sample containing additional lactic acid. Tissue samples (approximately 1.53 grams) were prepared and subjected to the prebiotic testing protocol described above. In certain instances lactic acid was added to the sample. In those instances where lactic acid was added, 0.5 mL of diluted lactic acid (1.25 mL of 80 percent lactic acid solution diluted to 1 L water) was added to the test sample. The final concentration of lactic acid in the sample was 0.01 percent. The various samples and the results of the prebiotic assay are described in the table below.

TABLE 2

| Sample | Creping Composition | Lactic Acid Addition (mg) | Ratio Inulin:LA | L. crispatus (Avg. CFU/Sample) | E. coli (Avg. CFU/Sample) | Ratio L. crispatus:E. coli |
|---|---|---|---|---|---|---|
| 1 | — | — | — | 522322 | 28254405 | 0.02 |
| 2 | — | 0.61 | — | 39685 | 43569 | 0.9 |
| 3 | Crepetrol 874/Inulin | — | — | 8355253 | 1454 | 5745 |
| 4 | Crepetrol 874/Inulin | 0.61 | 124:1 | 10544784 | 54 | 195778 |

Utilizing the tissue making process described above, additional samples were prepared to explore the range of prebiotic add-on, alternative creping compositions and the effect on tissue product properties. Alternative creping compositions included Crepetrol A9915 and Rezosol 6601 (both commercially available from Ashland Water Technologies, Wilmington, Del.). The samples were prepared using the creping compositions described below.

TABLE 3

| Code | Inulin (mg/m²) | Crepetrol 874 (mg/m²) | Crepetrol A9915 (mg/m²) | Rezosol 6601 (mg/m²) |
|---|---|---|---|---|
| 5 | — | — | — | — |
| 6 | 1174 | 5.14 | — | — |
| 7 | — | — | 1.4 | 4.2 |
| 8 | 5 | — | 0.9 | 4.2 |

The tissue samples were subjected to testing for prebiotic effect as described above. The results are summarized in the table below.

TABLE 4

| Sample | Creping Composition | L. crispatus (Avg. CFU/ sample) | E. coli (Avg. CFU/ sample) | Ratio L. crispatus:E. coli |
|---|---|---|---|---|
| 5 | — | 278334 | 115328299 | 0 |
| 6 | Crepetrol 874/Inulin | 8787034 | 1627 | 5400 |
| 7 | Crepetrol A9915/ Rezosol 6601 | 77681 | 3563583 | 0 |
| 8 | Crepetrol A9915/ Inulin/Rezosol 6601 | 16110434 | 1456236 | 11 |

The physical properties of the tissue samples were also evaluated, the results of which are summarized below.

TABLE 5

| Sample | Creping Composition | TS7 | Fine Crepe Structure (% COV at 200-390 μm) |
|---|---|---|---|
| 5 | — | 8.9 | 22.5 |
| 6 | Crepetrol 874/Inulin | 9.8 | 22.2 |
| 7 | Crepetrol A9915/ Rezosol 6601 | 10.3 | 22.8 |
| 8 | Crepetrol A9915/ Inulin/Rezosol 6601 | 11.1 | 21.8 |

In view of the foregoing description and examples, the present invention provides, in a first embodiment, a creped tissue web comprising greater than about 2 mg prebiotic per square meter of web surface area (mg/m$^2$), the web having a basis weight greater than about 10 gsm and a bulk greater than about 3 cc/g.

In a second embodiment the invention provides the tissue web of the first embodiment having a TS7 value less than about 10.

In a third embodiment the invention provides the tissue web of the first or second embodiments wherein the web has a basis weight from about 15 to about 30 gsm.

In a fourth embodiment the invention provides the tissue of any one of the first through third embodiments wherein the web has a geometric mean tensile (GMT) strength greater than about 500 g/3".

In a fifth embodiment the invention provides the tissue web of any one of the first through fourth embodiments wherein the creped tissue web further comprises an α-hydroxy acid.

In a sixth embodiment the invention provides the tissue web of any one of the first through fifth embodiments wherein the tissue web comprises from about 2 to about 1,000 mg/m$^2$ prebiotic selected from the group consisting of insulin, fructo-oligosaccharide (FOS), lactulose, galacto-oligosaccharide (GOS), raffinose, stachyose, isomalto-oligosaccharide, and xylo-oligosaccharide.

In a seventh embodiment the invention provides the tissue web of the fifth embodiment wherein the weight ratio of α-hydroxy acid to prebiotic agent is from about 1:1 to about 1:1,000.

In an eight embodiment the invention provides the tissue web of the first through the seventh embodiments having a TS7 value from about 8.0 to about 10.

In a ninth embodiment the invention provides the tissue web of the first through the eighth embodiments wherein the tissue web has a fine creped structure, measured as % COV at a wavelength from 200 to 390 μm, from about 20 to about 25.

In a tenth embodiment the invention provides a multi-ply tissue product comprising any one of the tissue webs of the first through ninth embodiments. In certain embodiments the foregoing multi-ply tissue product may have a basis weight from about 25 to 40 gsm and in other embodiments may have a GMT from about 500 to about 1,000 g/3".

In an eleventh embodiment the invention provides a method of manufacturing a prebiotic creped tissue web comprising the steps of dispersing cellulosic fibers to form a fiber slurry, forming a wet tissue web, partially dewatering the wet tissue web, applying a creping composition comprising a prebiotic to a creping cylinder, pressing the partially dewatered tissue web to the creping cylinder, drying the tissue web and creping the dried tissue web from the creping cylinder.

In a twelfth embodiment the invention provides the method of the eleventh embodiment wherein the creping composition further comprises an adhesive agent selected from the group consisting of polyvinyl alcohol, ethylene/vinyl acetate copolymer, animal glue, polyamidoamine-epichlorohydrin resins (PAE resins) and polyvinyl acetate and optionally a release agent selected from the group consisting of aliphatic polyols or oligomers thereof having a number average molecular weight of less than 600, polyalkanolamines, aromatic sulfonamides and pyrrolidone.

In a thirteenth embodiment the invention provides the method of the eleventh or twelfth embodiments wherein the creping composition further comprises water and the composition comprises from about 1 to about 100 mg/L prebiotic.

In a fourteenth embodiment the invention provides the method of anyone of the eleventh through thirteenth embodiments wherein the creping composition is applied to the creping cylinder at an add-on level from about 10 to about 2,000 mg per square meter of creping cylinder surface area.

In a fifteenth embodiment the invention provides the method of anyone of the eleventh through fourteenth embodiments wherein the creping composition further comprises an α-hydroxy acid selected from the group consisting of citric acid, lactic acid, methyllactic acid, phenyllactic acid, malic acid, mandelic acid, glycolic acid, tartronic acid, tartaric acid and gluconic acid.

In any one of the eleventh through fifteenth embodiments, the method of manufacture may yield a tissue web comprising greater than about 2 mg prebiotic per square meter of web surface area (mg/m$^2$), the web having a basis weight greater than about 10 gsm and a bulk greater than about 3 cc/g. In certain embodiments the foregoing tissue web may have a TS7 value less than about 10.

What is claimed is:

1. A tissue product comprising at least one creped tissue web having a basis weight greater than 10 grams per square meter (gsm) and a bulk greater than 3 cubic centimeters per gram (cc/g) and comprising at least 2 mg/m$^2$ prebiotic selected from the group consisting of inulin, fructo-oligosaccharide (FOS), lactulose and galacto-oligosaccharide (GOS) and an α-hydroxy acid.

2. The tissue product of claim 1 having a TS7 value less than 10.

3. The tissue product of claim 1 having a basis weight from 30 to 45 gsm and a geometric mean tensile (GMT) strength greater than 500 g/3".

4. The tissue product of claim 1 wherein the α-hydroxy acid is selected from the group consisting of citric acid, lactic acid, methyllactic acid, phenyllactic acid, malic acid, mandelic acid, glycolic acid, tartronic acid, tartaric acid and gluconic acid.

5. The tissue product of claim 1 wherein the prebiotic is insulin and the α-hydroxy acid is citric acid or lactic acid.

6. The tissue product of claim 1 wherein the tissue web comprises from 2 to 1,000 mg/m² prebiotic.

7. The tissue product of claim 1 wherein the weight ratio of α-hydroxy acid to prebiotic agent is from 1:1 to 1:1,000.

8. The tissue product of claim 1 having a GM Slope from 10 to 20 kgf and a stiffness index less than 18.

9. The tissue product of claim 1 having a basis weight from 30 to 45 gsm, a bulk from 3 to 8 cc/g, a GMT from 700 to a 1,000 g/3" and a TS7 value from 8.0 to 10.

10. A method of manufacturing a prebiotic creped tissue web comprising the steps of dispersing cellulosic fibers to form a fiber slurry, forming a wet tissue web, partially dewatering the wet tissue web, applying a creping composition comprising prebiotic selected from the group consisting of insulin, fructo-oligosaccharide (FOS), lactulose and galacto-oligosaccharide (GOS) and an α-hydroxy acid to a creping cylinder, pressing the partially dewatered tissue web to the creping cylinder, drying the tissue web and creping the dried tissue web from the creping cylinder.

11. The method of claim 10 wherein the creping composition further comprises an adhesive agent selected from the group consisting of polyvinyl alcohol, ethylene/vinyl acetate copolymer, animal glue, polyamidoamine-epichlorohydrin resins (PAE resins) and polyvinyl acetate and optionally a release agent selected from the group consisting of aliphatic polyols or oligomers thereof having a number average molecular weight of less than 600, polyalkanolamines, aromatic sulfonamides and pyrrolidone.

12. The method of claim 10 wherein the creping composition further comprises water and the composition comprises from 1 to 100 mg/L prebiotic.

13. The method of claim 10 wherein the creping composition is applied to the creping cylinder at an add-on level from 10 to 2,000 mg per square meter of creping cylinder surface area (mg/m²).

14. The method of claim 10 wherein the creping composition is applied to the creping cylinder at an add-on level greater than 1,000 mg/m².

15. The method of claim 10 wherein the α-hydroxy acid selected from the group consisting of citric acid, lactic acid, methyllactic acid, phenyllactic acid, malic acid, mandelic acid, glycolic acid, tartronic acid, tartaric acid and gluconic acid.

16. The method of claim 10 wherein the weight ratio of α-hydroxy acid to prebiotic agent is from 1:100 to 1:500.

17. The method of claim 10 wherein the prebiotic is insulin or fructo-oligosaccharide (FOS) and the α-hydroxy acid is citric acid or lactic acid.

18. The method of claim 10 wherein the web has a basis weight from 10 to 30 gsm, a geometric mean tensile (GMT) strength greater than 500 g/3" and a TS7 less than 10.

* * * * *

UNITED STATES PATENT AND TRADEMARK OFFICE
CERTIFICATE OF CORRECTION

| | | |
|---|---|---|
| PATENT NO. | : 9,744,248 B2 | Page 1 of 1 |
| APPLICATION NO. | : 15/367331 | |
| DATED | : August 29, 2017 | |
| INVENTOR(S) | : Michael Andrew Zawadzki et al. | |

It is certified that error appears in the above-identified patent and that said Letters Patent is hereby corrected as shown below:

In the Claims

Column 24, Line 21, Claim 17, replace "insulin" with "inulin".

Signed and Sealed this
Tenth Day of October, 2017

Joseph Matal
*Performing the Functions and Duties of the*
*Under Secretary of Commerce for Intellectual Property and*
*Director of the United States Patent and Trademark Office*